US012734026B2

(12) United States Patent
Hann et al.

(10) Patent No.: US 12,734,026 B2
(45) Date of Patent: Sep. 15, 2026

(54) 3D PRINTING OF BIOMIMETIC FLEXIBLE MULTILAYER BLOOD VESSELS

(71) Applicant: The George Washington University, Washington, DC (US)

(72) Inventors: Sung Yun Hann, Arlington, VA (US); Haitao Cui, Arlington, VA (US); Lijie Grace Zhang, Washington, DC (US)

(73) Assignee: The George Washington University, Washington, DC (US)

( * ) Notice: Subject to any disclaimer, the term of this patent is extended or adjusted under 35 U.S.C. 154(b) by 387 days.

(21) Appl. No.: 18/285,366

(22) PCT Filed: Apr. 8, 2022

(86) PCT No.: PCT/US2022/024094
§ 371 (c)(1),
(2) Date: Oct. 2, 2023

(87) PCT Pub. No.: WO2022/217104
PCT Pub. Date: Oct. 13, 2022

(65) Prior Publication Data

US 2024/0173117 A1 May 30, 2024

Related U.S. Application Data

(60) Provisional application No. 63/172,461, filed on Apr. 8, 2021.

(51) Int. Cl.
*A61F 2/06* (2013.01)
*A61L 27/22* (2006.01)
(Continued)

(52) U.S. Cl.
CPC ............ *A61F 2/062* (2013.01); *A61L 27/225* (2013.01); *A61L 27/3808* (2013.01);
(Continued)

(58) Field of Classification Search
CPC .... A61F 2/062; A61L 27/225; A61L 27/3808; A61L 27/3826; A61L 27/3891;
(Continued)

(56) References Cited

U.S. PATENT DOCUMENTS 10,857,260 B2 12/2020 Cui et al.
12,258,585 B2 * 3/2025 Kroll .................... C12N 5/0691
(Continued)

FOREIGN PATENT DOCUMENTS

WO 2019226710 A1 11/2019

OTHER PUBLICATIONS

International Search Report and Written Opinion issued Jun. 29, 2022 in counterpart International Application No. PCT/US2022/024094. 8 pages.
(Continued)

*Primary Examiner* — Bruce E Snow
(74) *Attorney, Agent, or Firm* — BLANK ROME LLP

(57) ABSTRACT

Systems and methods for producing artificial blood vessels. In certain embodiments, the method for producing blood vessels includes printing an elastic outer layer and removing polyvinyl alcohol component from the elastic outer layer. The process then involves forming a first inner layer of smooth muscle cells, wherein the smooth muscle cells are mixed with 5 fibrinogen solution and extruded with thrombin to form a smooth muscle cell gel, and forming a second inner layer of endothelial cells, wherein the endothelial cells are mixed with fibrinogen solution and extruded with thrombin to form an endothelial cell gel.

17 Claims, 15 Drawing Sheets

(51) Int. Cl.
*A61L 27/38* (2006.01)
*A61L 27/50* (2006.01)

(52) U.S. Cl.
CPC ....... *A61L 27/3826* (2013.01); *A61L 27/3891* (2013.01); *A61L 27/507* (2013.01)

(58) Field of Classification Search
CPC ....... A61L 27/507; A61L 27/56; B33Y 10/00; B33Y 80/00
See application file for complete search history.

(56) References Cited

U.S. PATENT DOCUMENTS

| | | | | |
|---|---|---|---|---|
| 2013/0164339 | A1 | 6/2013 | Murphy et al. | |
| 2019/0008998 | A1 | 1/2019 | Cui et al. | |
| 2020/0164109 | A1 * | 5/2020 | Kroll ...................... | B33Y 80/00 |

OTHER PUBLICATIONS

Piterina AV, Cloonan AJ, Meaney CL, Davis LM, Callanan A, Walsh MT, et al. ECM-based materials in cardiovascular applications: inherent healing potential and augmentation of native regenerative processes. International 20 journal of molecular sciences 2009;10:4375-417.

* cited by examiner

FIG. 10
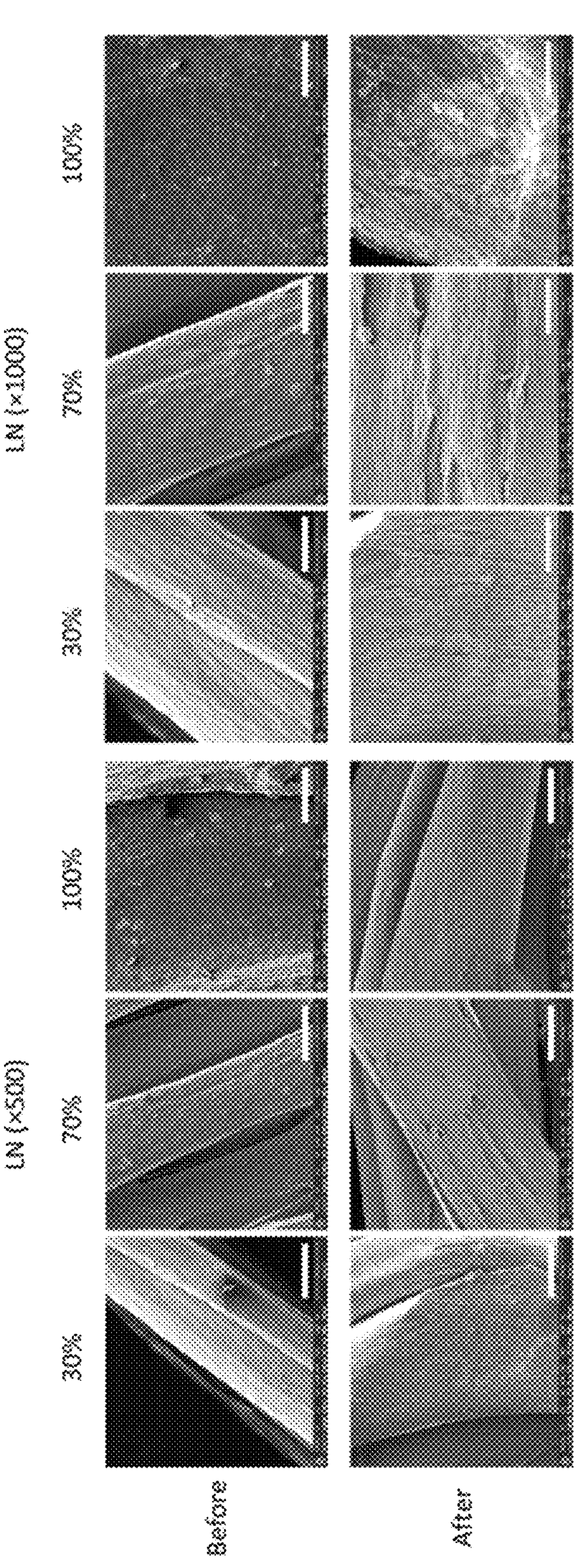
LN (×500)
LN (×1000)
30%
70%
100%
30%
70%
100%
Before
After

FIG. 12
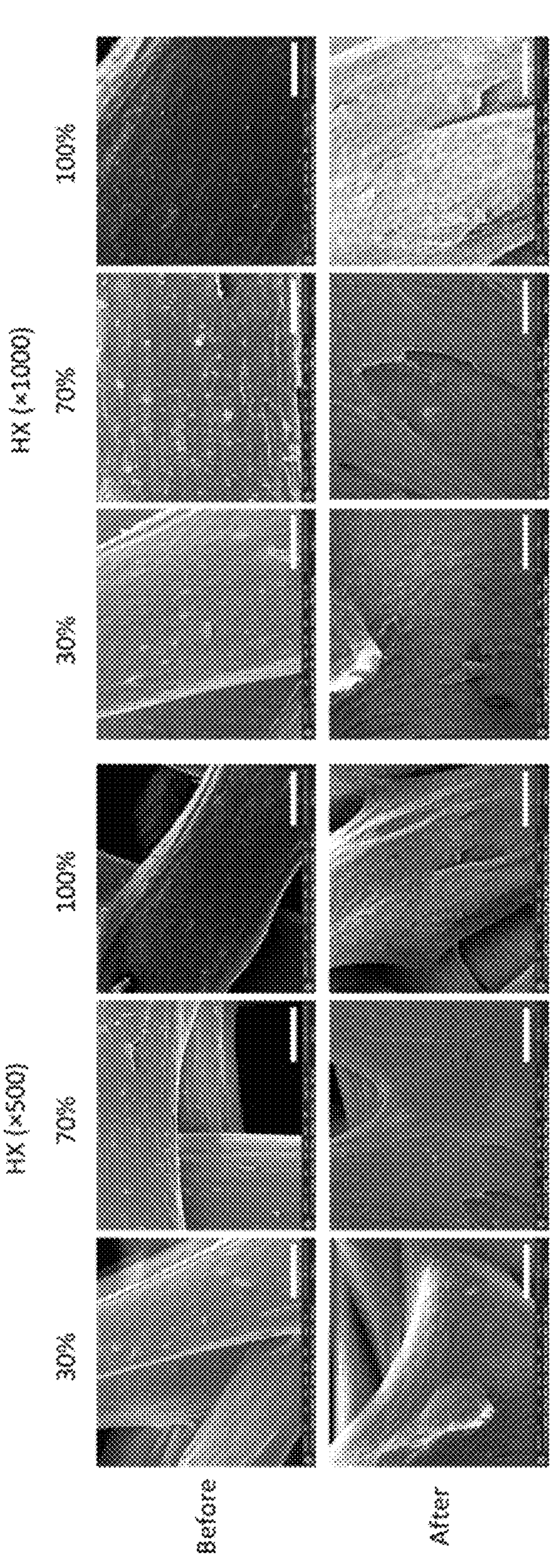

3D PRINTING OF BIOMIMETIC FLEXIBLE MULTILAYER BLOOD VESSELS

CROSS-REFERENCE TO RELATED APPLICATIONS

This application claims the benefit of PCT/US2022/024094, filed Apr. 8, 2022, which claims priority of U.S. Application Ser. No. 63/172,461 filed on Apr. 8, 2021, and entitled "3D Printing of Biomimetic Flexible Multilayer Blood Vessels," the content of which is relied upon and incorporated herein by reference in its entirety.

STATEMENT OF FEDERALLY SPONSORED RESEARCH OR DEVELOPMENT

This invention was made with government support under Grant No. 1854415 awarded by the National Science Foundation (NSF). The government has certain rights in the invention.

BACKGROUND OF THE INVENTION

Efforts have been made to artificially fabricate small-diameter (<6 mm) blood vessel grafts for biomedical applications due to the lack of available vascular autografts or artificial grafts. There are various tissue fabrication techniques. 3D printing has been widely gained attention for tissue and organ regeneration due to its outstanding reproducibility, repeatability, and controllability in replicating the complexity of native tissues. To fabricate 3D artificial blood vessels, polylactic acid (PLA) has been widely used as a filament material for fused deposition modeling (FDM) based 3D printing system due to its decent biocompatibility. However, PLA-based blood vessel grafts lack the flexibility to regulate blood flow during dilation and constriction. They also do not possess optimal porosity for nutrition exchange and oxygen diffusion for the neighbor tissues. Therefore, there is a need in the art to create elastic and bio-functional blood vessel grafts that can control blood flow and tolerate blood pressure with the vessel wall permeability barrier.

SUMMARY OF THE INVENTION

An aspect of this disclosure is a method for producing blood vessels comprising printing an elastic outer layer and removing a polyvinyl alcohol component from the elastic outer layer. The process then involves forming a first inner layer comprised of human induced pluripotent stem cell-derived smooth muscle cells, wherein the human induced pluripotent stem cell-derived smooth muscle cells are mixed with fibrinogen solution and extruded with thrombin to form a smooth muscle cell gel, and forming a second inner layer comprised of human induced pluripotent stem cell-derived endothelial cells, wherein the human induced pluripotent stem cell-derived endothelial cells are mixed with fibrinogen solution and extruded with thrombin to form an endothelial cell gel.

In some embodiments, the polyvinyl alcohol is removed by immersing the elastic outer layer in deionized water.

In other embodiments, the outer layer is comprised of a biodegradable elastomer.

In yet other embodiments, the blood vessel has high elasticity and porosity.

In certain other embodiments, the first inner layer is between the outer layer and the second inner layer.

In other embodiments, the iSMCs are first mixed with the fibrinogen solution and then coaxially extruded with the thrombin.

In certain other embodiments, the iECs are first mixed with the fibrinogen solution and then coaxially extruded with the thrombin.

This summary is not intended to identify all essential features of the claimed subject matter, nor is it intended for use in determining the scope of the claimed subject matter. It is to be understood that both the foregoing general description and the following detailed description are exemplary and are intended to provide an overview or framework to understand the nature and character of the disclosure.

BRIEF DESCRIPTION OF THE FIGURES

The accompanying drawings are incorporated in and constitute a part of this specification. It is to be understood that the drawings illustrate only some examples of the disclosure and other examples or combinations of various examples that are not specifically illustrated in the figures may still fall within the scope of this disclosure. Examples will now be described with additional detail through the use of the drawings, in which:

FIG. 10 shows SEM images of 3D printed scaffolds using a linear printing pattern with different infill densities at ×500 and ×1000 magnifications before (top row) and after (bottom row) PVA removal. Scale bars, 200 μm and 100 μm for ×500 and ×1000 magnifications, respectively. Scale bars: 200 μm for ×500 and 100 μm for ×1000;

FIG. 12 shows SEM images of 3D printed scaffolds using a hexagonal printing pattern with different infill densities at ×500 and ×1000 magnifications before (top row) and after (bottom row) PVA removal. Scale bars, 200 μm and 100 μm for ×500 and ×1000 magnifications, respectively. Scale bars: 200 μm for ×500 and 100 μm for ×1000;

Figure 1:
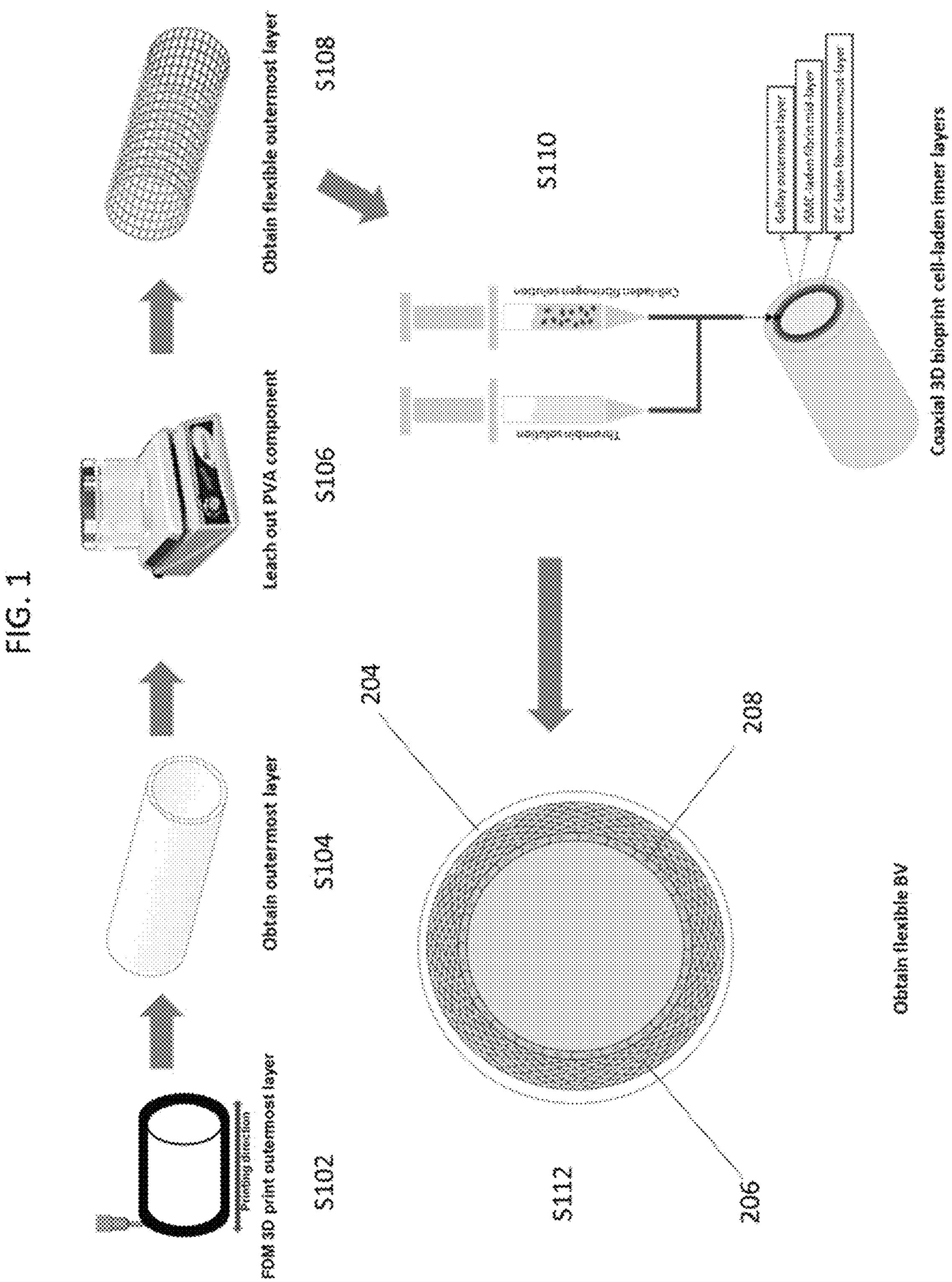
FIG. 1 is a diagram of a method for the producing blood vessel in accordance with an exemplary embodiment.

The figures show illustrative embodiments of the present disclosure. Other embodiments can have components of different scale. Like numbers used in the figures may be used to refer to like components. However, the use of a number to refer to a component or step in a given figure has a same structure or function when used in another figure labeled with the same number, except as otherwise noted.

DETAILED DESCRIPTION OF THE PREFERRED EMBODIMENTS

In describing the illustrative, non-limiting embodiments illustrated in the drawings, specific terminology will be resorted to for the sake of clarity. However, the disclosure is not intended to be limited to the specific terms so selected, and it is to be understood that each specific term includes all technical equivalents that operate in similar manner to accomplish a similar purpose. Several embodiments are described for illustrative purposes, it being understood that the description and claims are not limited to the illustrated embodiments and other embodiments not specifically shown in the drawings may also be within the scope of this disclosure.

Development of artificial blood vessels is a time-intensive process. The need for artificial blood vessels is high, and blood vessels must meet several characteristics in order to be clinically viable. The artificial blood vessel replicates the characteristics of a live blood vessel in that it has the same or similar flexibility to a live blood vessel. In addition to the mechanical properties, the blood vessel of the present technology mimics the structure of a live blood vessel, such as having distinctive inner layers (smooth muscle and endothelium). Further, the fabrication of a flexible blood vessel is beneficial compared to a rigid one because it possesses greater adaptability to repair a damaged blood vessel in the human body. For instance, the rigid blood vessel can be designed and used for the particular region, while the flexible ones, as produced using the present technology, have no such limitation. For example, blood vessels must exhibit compatibility and no thrombosis, possess sufficient mechanical properties and strength, exhibit good biodegradability and tissue regeneration ability, show no toxicity and no immunologic rejection, and possess a simple preparation method.

The present technology describes artificial blood vessels with superior flexibility, stretchability (preferably up to 262% elongation), and durability to endure high blood pressure, ensuring the physiological function of vasodilation and vasoconstriction that occurs in native vessels. The technology further describes innovative dual 3D printing system (fused deposition modeling and coaxial bioplotting), associated with different printable materials to satisfy the required structure, dimensions, mechanics, and biofunctionality. Furthermore, since the fibrinogen and thrombin as well as fibrin used in the method for production are the natural components of the human blood, the design provides an optimal condition for blood vessel cells.

FIG. 1 is a diagram of a device and method for the producing blood vessel in accordance with an exemplary embodiment. The method for producing blood vessels of the present technology commences at step S102, where an outer layer for the blood vessel is printed. At step S104, the unfinished outer layer 204 is obtained. The outer layer 204 is preferably substantially tubular in shape and may have any diameter that is acceptable for use, as determined by one of ordinary skill in the art. The outer layer is preferably comprised of an elastomer. The outer layer 204 functions as elastic support to increase the mechanical tolerance of high blood pressure. In certain embodiments, the outer layer 204 is printed using a using a 3D fused deposition modeling (FDM) printer.

At step S106, the PVA component is leached out of the printed outer layer. In certain embodiments, the process is performed by immersing the scaffolds in deionized water ($dH_2O$) to obtain the aligned microgroove pattern with a porous surface and/or with a rough surface or the structure can have other interruptions such as holes or slots, which are beneficial for cell adhesion and arrangement. The rough surface can be, for example, that the surface can have pits, grooves, dimples, or the like. In some embodiments, the interruptions can have irregular shapes. Following that leaching process, at step S108, a flexible outermost layer 204 (which is also the outer layer of the blood vessel) is obtained. The leaching of PVA (step S106) is complete when the roughness of the surface of the outer layer 204 or interruptions are sufficient when the desired level of elasticity and porosity is reached for the outer layer. The structure shown in FIG. 1 is illustrative only and any structure can be obtained, though in this case, the structure may be tubular with a circular cross-section.

At step S110, two distinct cell-laden inner layers are created, i.e., endothelium and smooth muscle. This can be done, for example, using a coaxial needle such as the one shown in U.S. Pat. No. 10,857,260, the entire contents of which are hereby incorporated by reference; though any suitable method and device can be utilized. In certain embodiments, a coaxial-bioplotting 3D printer (also known as a coaxial bioplotter) is used to create the two inner layers. In some cases, the two inner layers may be comprised of two layers of fibrin gel with two different cell lines comprised of smooth muscle cells and endothelial cells. In certain embodiments, those cells may be human induced pluripotent stem cell-derived smooth muscle cells (iSMCs) and human induced pluripotent stem cell-derived endothelial cells (iECs). These cell lines are formed by the combination of thrombin (an enzyme) and fibrinogen (a protein).

In various embodiments, smooth muscle cells or endothelial cells are blended with a fibrinogen solution first, then coaxially extruded with thrombin to form a cell-laden gel. The gels formed may be a smooth muscle cell gel and an endothelial cell gel. In certain embodiments, the process uses a coaxial needle that can apply the two different gels (i.e., the smooth muscle cell gel and endothelial cell gel) either simultaneously or sequentially without having to change needles. The coaxial needle may apply the smooth muscle cell gel along a portion of, or the complete length of the outermost layer, then may apply the endothelial cell gel along a portion of, or the complete length of the smooth muscle cell layer.

In some embodiments, application of the endothelial cell gel may be performed after some delay following application of the smooth muscle cell gel to allow for the smooth muscle cell gel to cure and thereby avoid mixing of the two smooth muscle cell gel with the endothelial cell gel. Delay between application of the smooth muscle cell gel and endothelial cell gel may be, for example, approximately one (1) minute, though can also be greater or less than one minute. In some embodiments, the first gel comprised of smooth muscle cells is injected before the second gel comprised of endothelial cells using a normal needle (not a coaxial needle). Using that process, at step S112, a blood vessel in accordance with the present technology is obtained.

Figure 2:
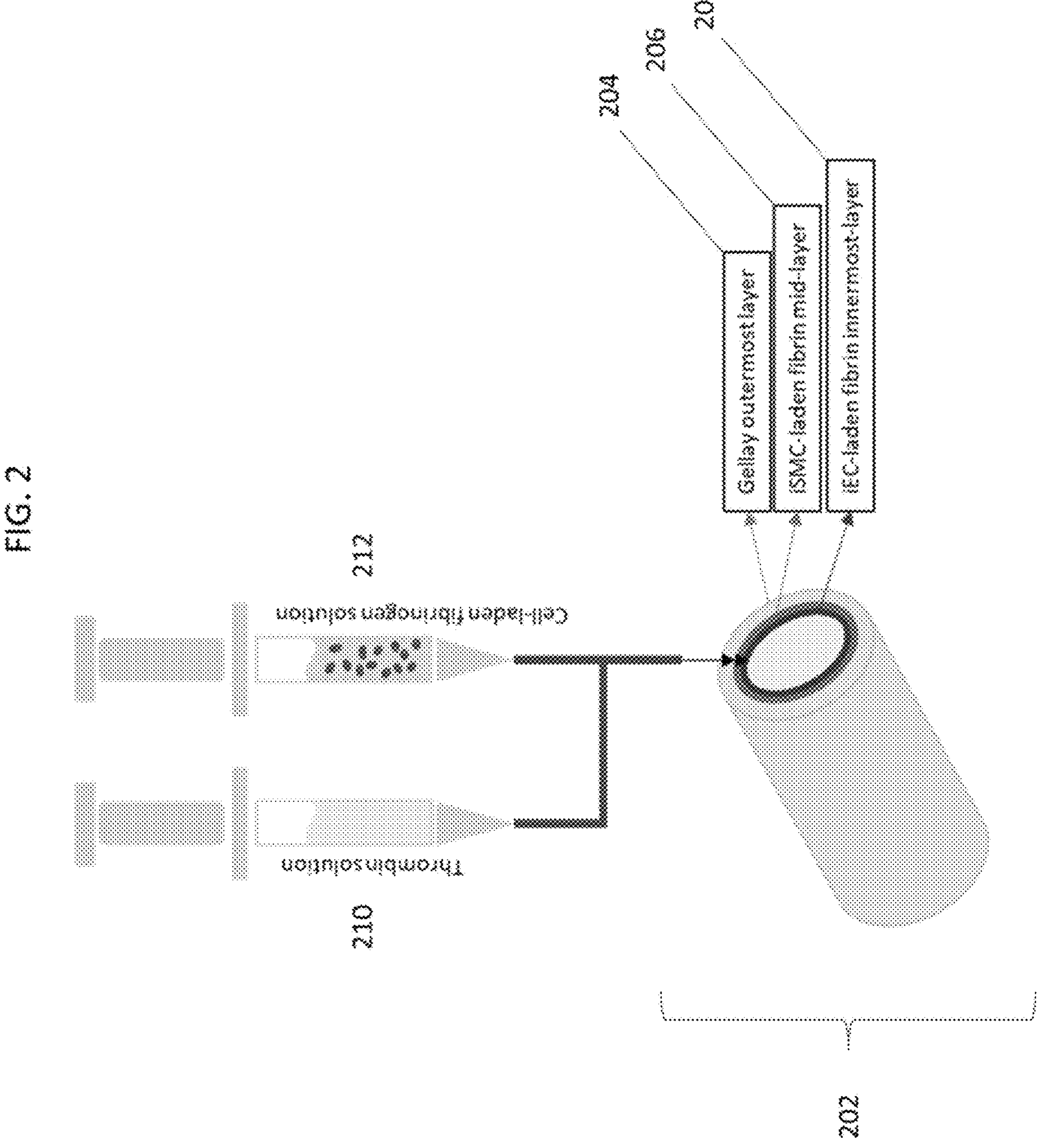
FIG. 2 is a diagram of a biomimetic flexible multilayer blood vessel in accordance with an exemplary embodiment.

FIG. 2 is a diagram of a biomimetic flexible multilayer blood vessel in accordance with an exemplary embodiment, showing in greater detail the operation of step S110 of FIG. 1. As shown, the blood vessel 202 is comprised of three layers: an outer layer 204, which is preferably comprised of a rubber-like elastomer (e.g., Gellay), an iSMC-laden fibrin mid-layer 206 (i.e., the smooth muscle cell gel), and an iEC-laden fibrin innermost layer 208 (i.e., the endothelial cell gel). Each layer 204, 206, 208 has a tubular shape and forms a discrete continuous uninterrupted body with a circular cross-section. The layers 204, 206, 208 are concentric with respect to one another, such that the inner layer 204 has the smallest diameter, the mid-layer 206 has a larger diameter than the inner layer 204, and the outer layer 204 has a larger diameter than the inner layer 204 and the mid-layer 206; whereby the mid-layer 206 is sandwiched between the outer layer 204 and the inner layer 208. In addition, the layers 204, 206, 208 are bonded together or integrally formed to be continuous with one another to form a discrete and uniform body. That is, the outer surface of the inner layer 208 is bonded to or integrally formed with the inner surface of the mid-layer 206, and the outer surface of the mid-layer 206 is bonded to or integrally formed with the inner surface of the outer layer 204. The mid-layer 206 and the inner layer 208, which are comprised of fibrin hydrogel in certain embodiments, will bond to each other using their innate viscoelastic property.

The outer layer 204 works as a protective layer to maintain the entire shape of the construct. The mid-layer 206 and the inner layer 208 are smooth muscle and endothelium that mimic a live blood vessel. Fewer or more layers may be used if the resolution of a 3D printer permits and per the needs of the patient. In certain embodiments, each layer is approximately 10-20 μm thick. Thicker or thinner layers can be also fabricated depending on the printer type and the needs of the patient. For the length of the blood vessel, there is no limitation as long as sufficient cell numbers and biomaterials are provided.

As explained with regard to FIG. 1, the iSMC-laden fibrin mid-layer 206 and the iEC-laden fibrin innermost layer 208 are preferably formed at step S110 of FIG. 1 using a combination of thrombin solution 210 and a cell-laden fibrinogen solution 212, where the fibrinogen solution is comprised of iSMCs or iECs.

Figures 3A, 3B:
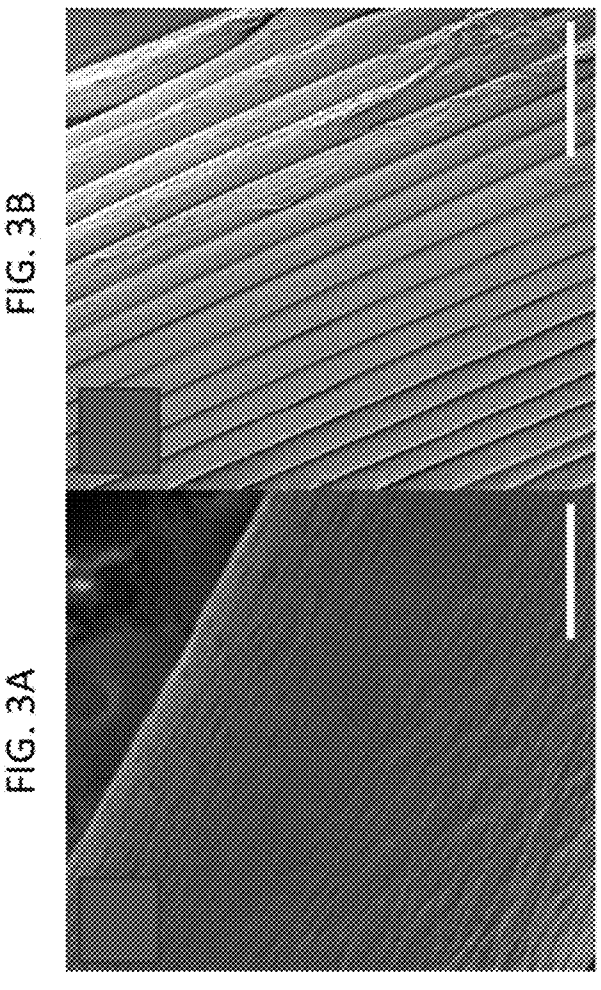
FIG. 3A is an SEM images of the outer layer of the biomimetic flexible multilayer blood vessel before leaching out PVA. Scale bars, 500 μm.
FIG. 3B is an SEM images of the outer layer of the biomimetic flexible multilayer blood vessel after leaching out PVA. Scale bars, 500 μm.

FIG. 3A is an SEM image of the outer layer (FIG. 1, step S104) of the biomimetic flexible multilayer blood vessel before leaching out PVA (FIG. 1, step S106). FIG. 3B is another SEM image of the outer layer 204 (FIG. 1, step S108) of the biomimetic flexible multilayer blood vessel after leaching out PVA. Both of these figures demonstrate that the vessels of the present technology result in high elasticity and porosity as is visible in the SEM images. FIG. 4 demonstrates that the flexibility improves after leaching out the PVA component. FIGS. 3A and 3B indicate the surface morphology change. In FIG. 3B, the filament is aligned with the direction of elongation, therefore, it is evidence of the enhanced flexibility after leaching out the PVA component.

Further, as demonstrated in Table 1 below, the elastic modulus of the vessels produces is nearly the same as the native carotid artery of men. See Piterina A V, Cloonan A J, Meaney C L, Davis L M, Callanan A, Walsh M T, et al. ECM-based materials in cardiovascular applications: inherent healing potential and augmentation of native regenerative processes. International journal of molecular sciences 2009; 10:4375-417. In certain embodiments, before PVA removal, the tensile modulus is preferably between 80 and 91 MPa., while the elongation at break percentage is preferably between 110 and 117%. In embodiments, after PVA removal, the tensile modulus is preferably between 0.54 and 0.67 MPa, while the elongation at break percentage is preferably between 254 and 271%.

TABLE 1

| | Tensile Modulus (MPa) | Elongation at Break (%) |
|---|---|---|
| Before PVA Removal | 86.62 | 113.82 |
| After PVA Removal | 0.62 | 262.67 |
| Native BV (Carotid Artery of men) | 0.607 | N/A |

Figure 4A:
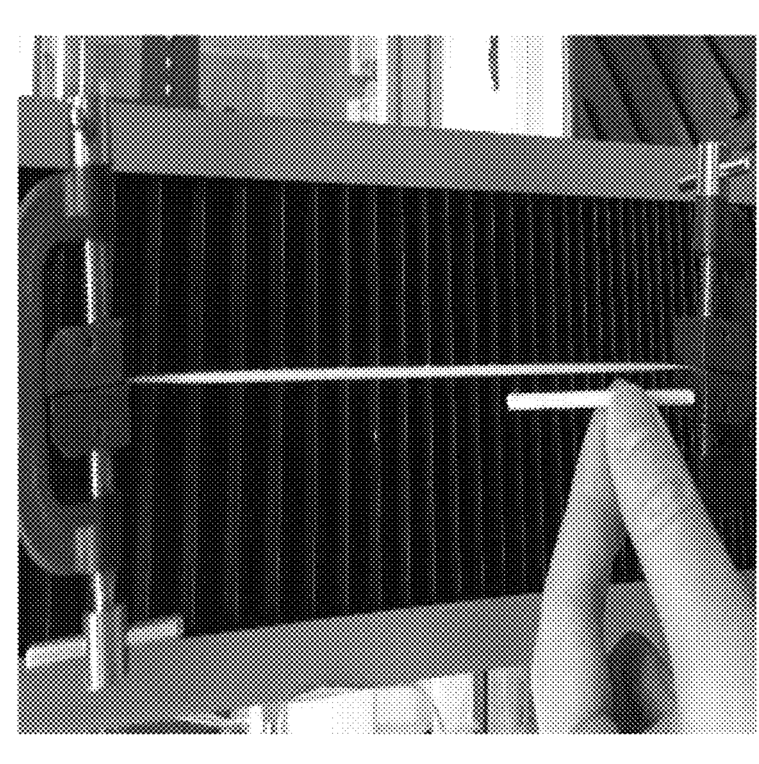
FIG. 4A is a photograph of the biomimetic flexible multilayer blood vessel.
Figure 4B:
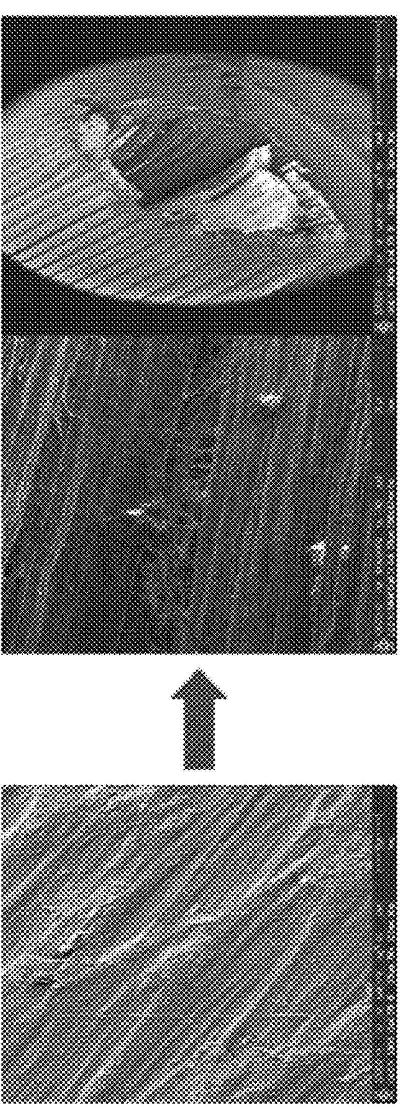
FIG. 4B is an SEM images of the biomimetic flexible multilayer blood vessel.

FIG. 4A is a photograph of the biomimetic flexible multilayer blood vessel, while FIG. 4B is an SEM image of the biomimetic flexible multilayer blood vessel. As is the case with respect to FIGS. 3A and 3B, these figures show that the blood vessels produced using the present technology are porous and elastic. In FIG. 4A, the scaffolding shown corresponds to the product shown in S104 (before leaching out PVA) in FIG. 1 and the leftmost image in FIG. 4B. The right two images in FIG. 4B correspond to S108 (after leaching out PVA). FIG. 4A indicates the flexibility difference before and after PVA leaching. These images show that the surface roughness has changed after leaching out PVA.

Figure 5:
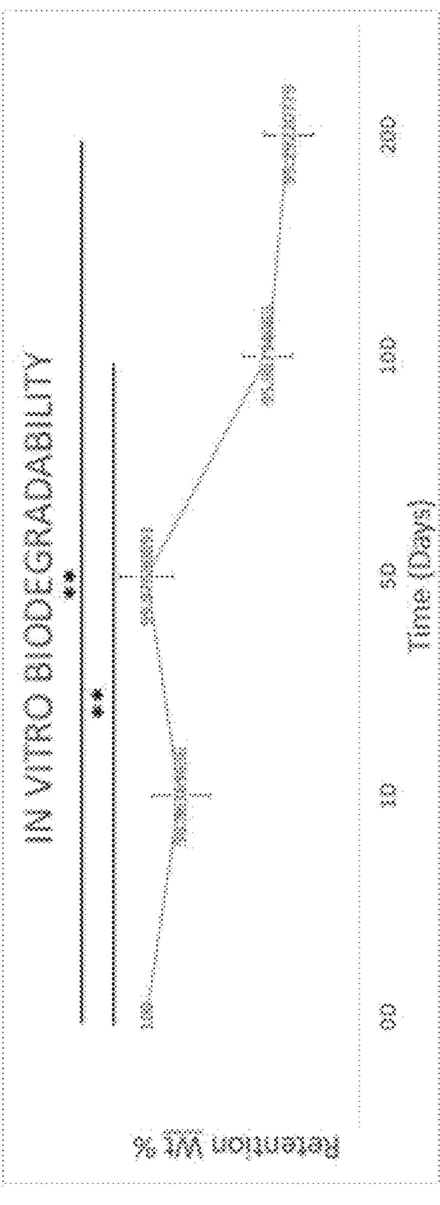
FIG. 5 is a chart showing the in vitro biodegradability of the blood vessel elastomer outer layer of the blood vessel.

FIG. 5 is a chart showing the in vitro biodegradability of the blood vessel elastomer outer layer of the blood vessel. As FIG. 5 shows, the blood vessel biodegrades over the twenty-day period examined from 100% of its weight to 95.29% of its weight. This biodegradability is favorable because the scaffolds provide the optimal templates prior to the complete regeneration of biologically functional blood vessel.

Figure 6:
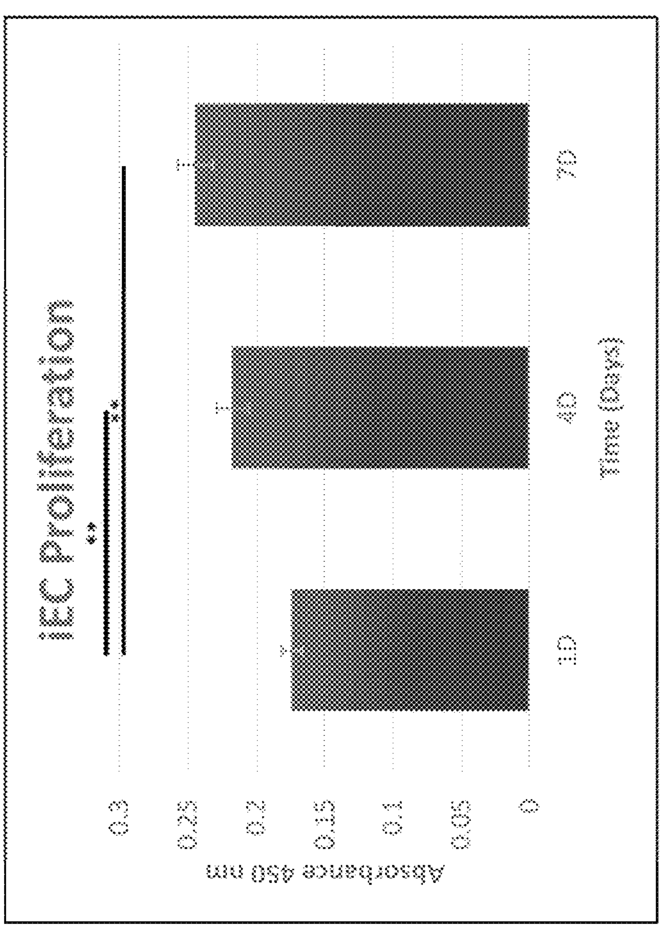
FIG. 6 is a chart showing iEC proliferation in the blood vessel over 1, 4, and 7 days.
Figure 7:
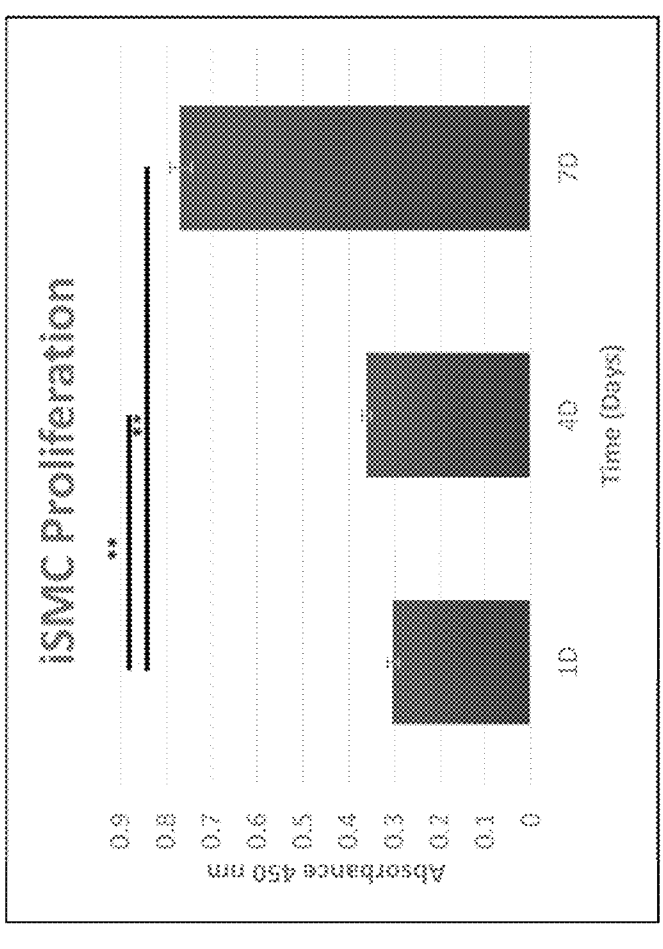
FIG. 7 is a chart showing iSMC proliferation in the blood vessel over 1, 4, and 7 days.
Figure 8:
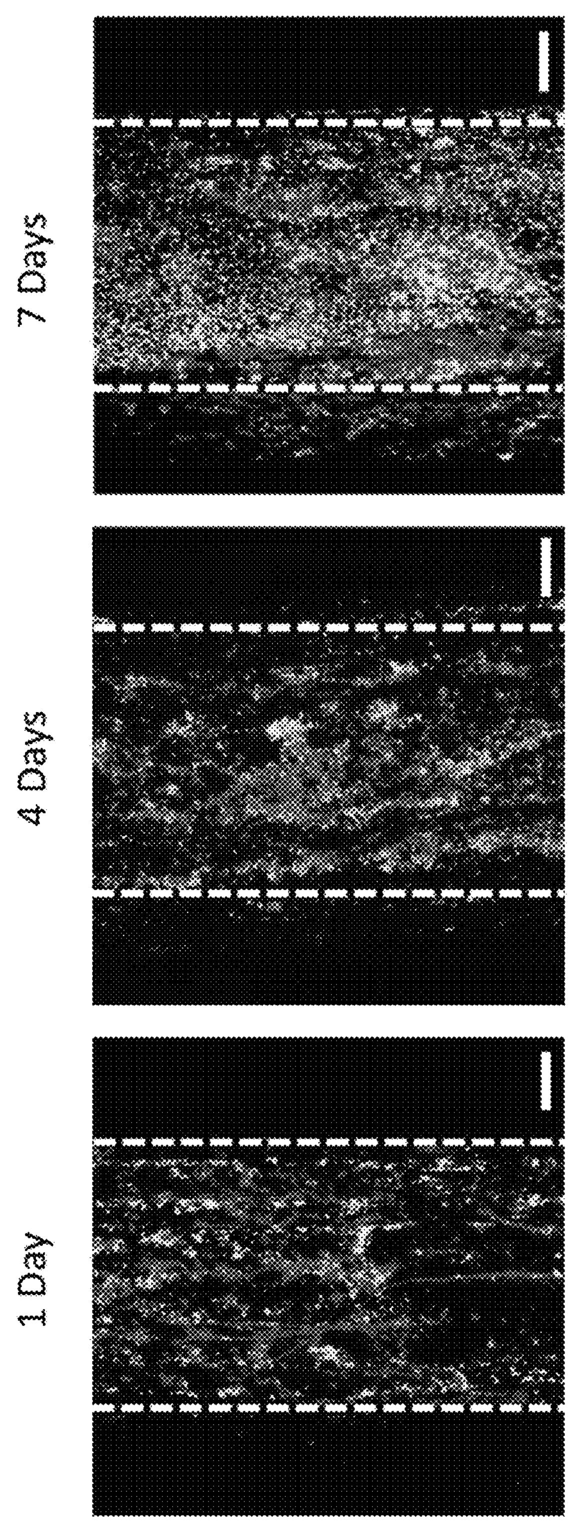
FIG. 8 shows images of iSMC (Red) and iEC (Green) proliferation in the blood vessel over 1, 4, and 7 days. Scale bars, 500 μm.

FIG. 6 is a chart showing iEC proliferation in the blood vessel over 1, 4, and 7 days, while FIG. 7 is a chart showing iSMC proliferation in the blood vessel over 1, 4, and 7 days. Similarly, FIG. 8 shows images of iSMC and iEC proliferation in the blood vessel over 1, 4, and 7 days. The charts of FIGS. 6 and 7 show that the iSMCs in the iSMC-laden fibrin mid-layer 206 and the iECs in the iEC-laden fibrin innermost layer 208 proliferate effectively in blood vessels produced using the present technology, with iECs increasing from just under 0.2*2400 cells/mm$^2$ to almost 0.25*2400 cells/mm$^2$ from Day 1 to Day 7, while iSMCs increase from 0.3*1200 cells/mm$^2$ to almost 0.8*1200 cells/mm$^2$ from Day 1 to Day 7. As shown, 2400 and 1200 cells/mm$^2$ refer to the number of initially seeded cells. The y-axis indicates relative proliferation rate. An increase in the cell proliferation rate over time is favorable since it is an important marker to prove the biocompatibility of our materials.

Figures 9A, 9B, 9C:
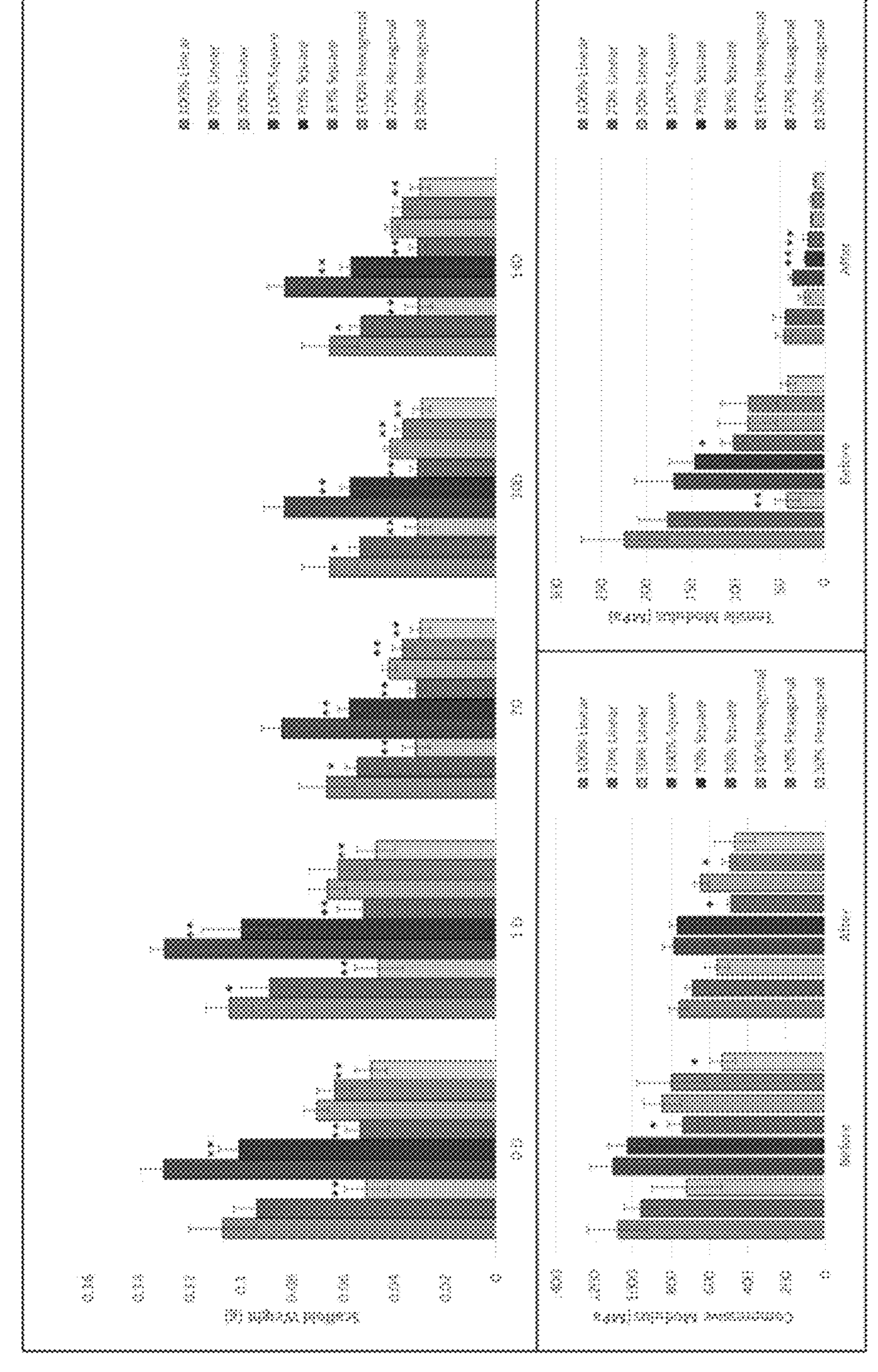
FIG. 9A is a bar chart showing weight change quantification of the 3D printed scaffolds with different infill densities (30%, 70%, and 100%) and different printing patterns (Linear, Square, and Hexagonal) during the PVA leaching out process.
FIG. 9B is a bar chart showing compressive moduli of the 3D printed scaffold before and after PVA removal.
FIG. 9C is a bar chart showing tensile moduli of the 3D printed scaffold before and after PVA removal. *:$p<0.05$ and **:$p<0.01$ when compared to 100% groups of the same printing pattern. N=9.

FIG. 9A is a bar chart showing weight change quantification of the 3D printed scaffolds with different infill densities (30%, 70%, and 100%) and different printing patterns (Linear, Square, and Hexagonal) during the PVA leaching out process. FIG. 9B is a bar chart showing compressive moduli of the 3D printed scaffold before and after PVA removal. FIG. 9C is a bar chart showing tensile moduli of the 3D printed scaffold before and after PVA removal. As summarized in FIGS. 9A-9C, to optimize and characterize the printing material, groups of 3D printed rubber-like elastomer scaffolds with 100%, 70%, and 30% infill densities and linear, square, and hexagonal printing patterns (total 9 groups) were prepared to test weight change during the PVA removal process and to measure compressive/tensile moduli before and after PVA removal.

Figure 11:
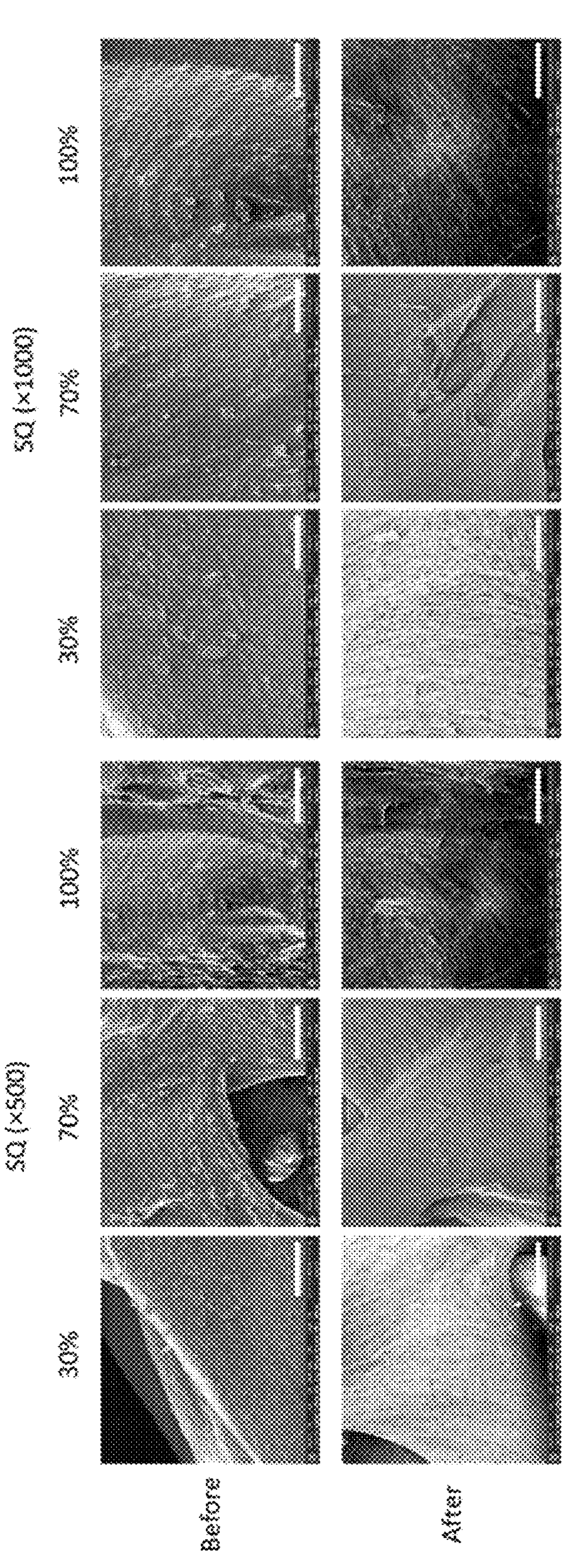
FIG. 11 shows SEM images of 3D printed scaffolds using a square printing pattern with different infill densities at ×500 and ×1000 magnifications before (top row) and after (bottom row) PVA removal. Scale bars, 200 μm and 100 μm for ×500 and ×1000 magnifications, respectively. Scale bars: 200 μm for ×500 and 100 μm for ×1000.

FIGS. 10-12 are SEM images showing various printing patterns. FIG. 10 shows SEM images of 3D printed scaffolds using a linear printing pattern with different infill densities at ×500 and ×1000 magnifications before (top row) (FIG. 1, step S104) and after (bottom row) (FIG. 1, step S108) PVA removal. FIG. 11 shows SEM images of 3D printed scaffolds using a square printing pattern with different infill densities at ×500 and ×1000 magnifications before (top row) and after (bottom row) PVA removal. FIG. 12 shows SEM images of 3D printed scaffolds using a square printing pattern with different infill densities at ×500 and ×1000 magnifications before (top row) and after (bottom row) PVA removal. FIGS. 10-12 show that the surface morphology changes (surface area) before and after leaching out PVA in all groups during the optimization process. It appears that the surface roughness (surface area) changes occur in all the groups. Then, going back to FIGS. 9A-C, based on the quantification of weight change and moduli, Linear (Printing pattern) with 100% (Printing infill density) group was chosen for the fabrication of the flexible blood vessel.

FIGS. 9-12 establish that the removal of PVA resulted in a higher surface area in all 9 groups, regardless of printing pattern and infill density. As shown in FIGS. 9A-9C, scaffold weight decreased across all groups, along with their compressive moduli and tensile moduli. These results demonstrate that it can take up to 14 days to completely remove PVA (FIG. 9A), and all the groups still possess proper mechanical properties even after the PVA removal (FIGS. 9B and 9C). Depending on the dimensions of the blood vessel produced, the PVA removal process may preferably take from 10 to 14 days (for a vessel having a 2-50 mm diameter). In certain embodiments, the PVA removal process may be sped up by increasing the temperature of the deionized water. Preferably, the temperature of the deionized water may be up to approximately 80° C. Among them, the linear 100% group is the optimal choice for the fabrication of 3D flexible blood vessel since it demonstrates the most outstanding tensile and compressive moduli (FIGS. 9B and 9C).

Figure 13:
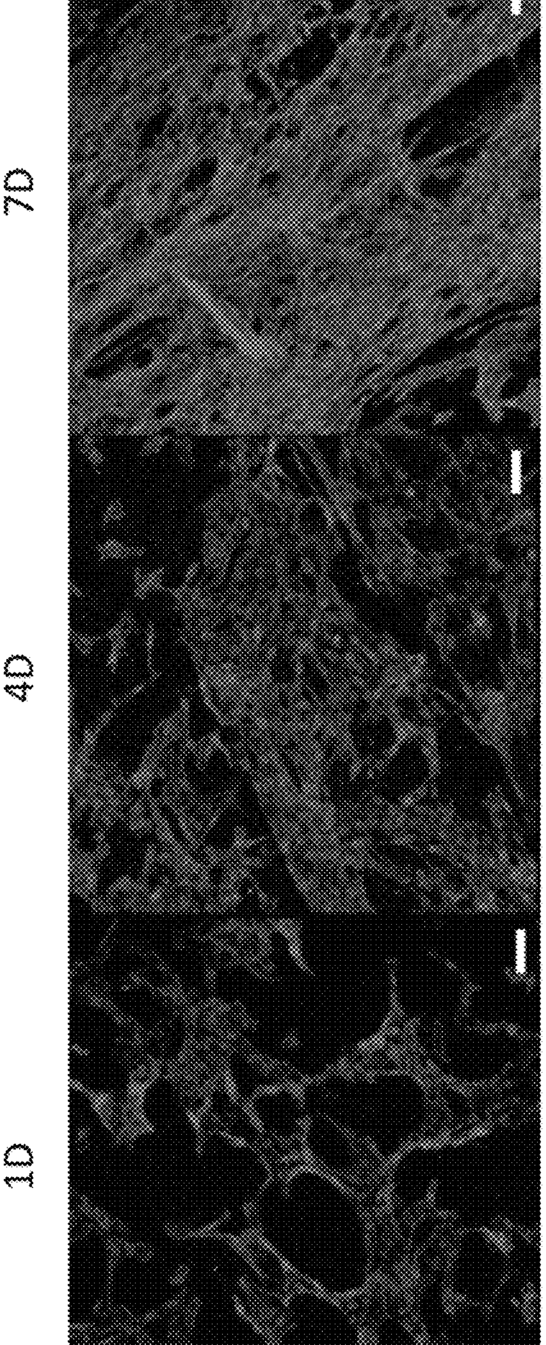
FIG. 13 shows confocal images (F-actin staining) of iSMCs after 1, 4, and 7 days embedded in the fibrin gel layer. Scale bars: 100 μm.
Figure 14:
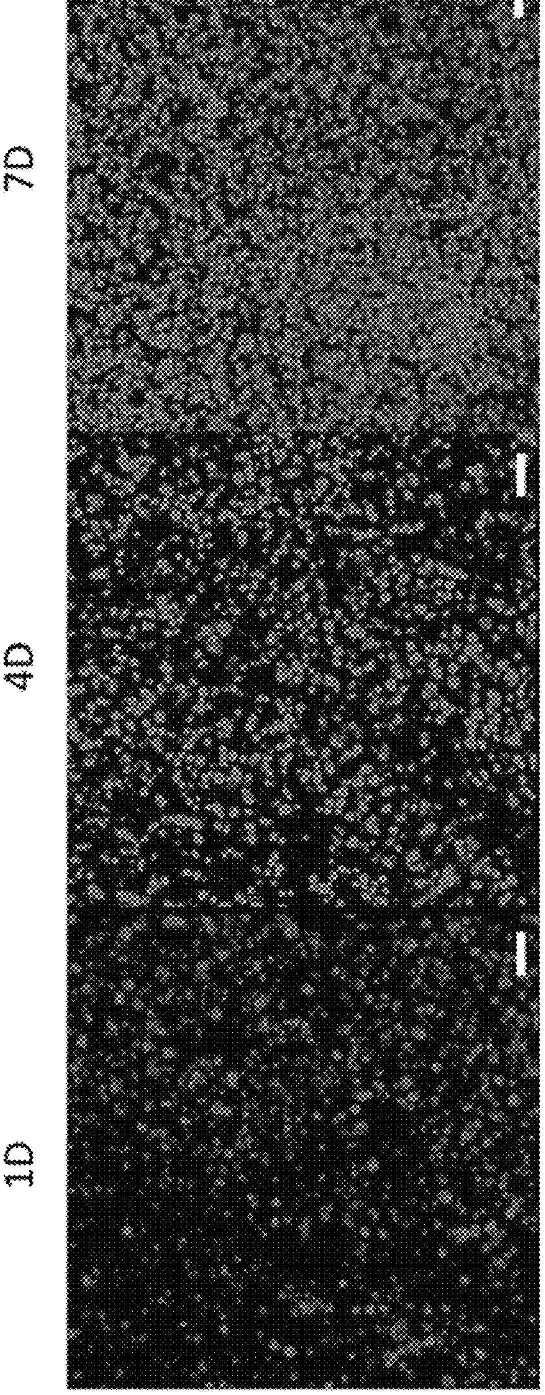
FIG. 14 shows confocal microscope images (F-actin staining) of iECs after 1, 4, and 7 days of seeding. Scale bars: 100 μm.

FIG. 13 shows confocal images (F-actin staining) of iSMCs after 1, 4, and 7 days embedded in the fibrin gel layer, while FIG. 14 shows confocal microscope images (F-actin staining) of iECs after 1, 4, and 7 days of seeding. These figures demonstrate the effective proliferation of iSMCs and iECs in the blood vessels produced using the present technology. The images further show the cell growth and morphology. From these results, it can be confirmed that the low biocompatibility of the outer layer does not affect the cell viability due to the presence of fibrin gel. In order to culture iPSCs, the selection of biomaterial is one element to consider because the cells are very material-specific to grow. This is one deficiency in the art that was overcome using the present technology.

As used herein, elasticity generally refers to the capability of stretching so as to return to an original shape, while flexibility refers to how easily an object is deformed. The blood vessel model can stretch up to ~260% of its original length, as shown in Table 1 above. Most of the previous studies designed and fabricated a blood vessel model using rigid polymers; whereas the present disclosure fabricates a small-diameter blood vessel with complex design. Also, a live blood vessel is designed not rigid, but flexible to perform dilation and constriction to allow the circulatory system to change the amount of blood flowing.

The present blood vessel resembles the features of a native blood vessel. The innate material property of the outer layer allows the blood vessels of the present technology to achieve the desired flexibility, durability, stretchability, elasticity, and porosity needed to mimic a native blood vessel. The outer layer 204 (which is the outermost layer of the vessel) is less flexible than the inner and mid layers, and therefore the outer layer 204 defines the flexibility of the produced blood vessel. In certain embodiments, the outer layer 204 may be printed parallel to the longitudinal axis of the blood vessel, as shown by the directional arrow 50 in FIG. 1. That is, for a vessel having a length of 50 mm, the printer prints in the longitudinal direction. In other words, the printer prints 50 mm long lines at a time, which becomes a circular tube when the printing is complete. Printing in the longitudinal direction 50 improves the flexibility of the outer layer 204 in the longitudinal direction, so that the outermost layer 204 can stretch in the longitudinal direction. In general, ~140 mm Hg of human blood pressure is considered very high, which is equal to ~17 kPa. According to the modulus testing data, the blood vessel of the present technology is in the range of MPa for both tensile and compressive moduli, which is more than 1,000 times greater than the blood pressure, demonstrating that it is more than capable of handling the pressure requirements.

The blood vessels of the present technology may be produced in a variety of sizes and lengths. In one example embodiment, the dimension is 2 mm (D)×50 mm (L). However, larger or smaller scaffolds may be fabricated. In certain embodiments, the produced vessel is preferably equal to or narrower than 6 mm in diameter. Furthermore, depending on the blood vessel to be produced, the middle layer may be optional, and therefore removed or eliminated. Or, as iPSCs are material-specific to culture, in certain embodiments, collagen may be used instead.

It is noted that the drawings may illustrate, and the description and claims may use geometric or relational terms, such as inner, outer, tubular, concentric, circular. These terms are not intended to limit the disclosure and, in general, are used for convenience to facilitate the description based on the examples shown in the figures. In addition, the geometric or relational terms may not be exact. For instance, layers may not be exactly concentric to one another because of, for example, roughness of surfaces, tolerances allowed in manufacturing, etc., but may still be considered to be concentric.

It should be understood at the outset that although illustrative implementations of the embodiments of the present disclosure are illustrated, the present invention may be implemented using any number of techniques, whether currently known or in existence. The present disclosure should in no way be limited to the illustrative implementations, drawings, and techniques illustrated, including the exemplary design and implementation illustrated and described herein, but may be modified within the scope of the appended claims along with their full scope of equivalents.

The invention claimed is:

1. A method for producing a blood vessel comprising:

printing an outer layer;

removing a polyvinyl alcohol component from the outer layer to produce an elastic outer layer;

forming a first inner layer comprised of smooth muscle cells comprised of smooth muscle cell gel comprised of smooth muscle cells, fibrinogen, and thrombin, wherein the smooth muscle cells are first mixed with a fibrinogen solution and then coaxially extruded with the thrombin; and forming a second inner layer comprised of an endothelial cell gel comprised of endothelial cells, a fibrinogen, and thrombin, wherein the first inner layer is between the elastic outer layer and the second inner layer.

2. The method of claim 1, wherein the polyvinyl alcohol is removed by immersing the elastic outer layer in deionized water.

3. The method of claim 1, wherein the outer layer is comprised of a biodegradable elastomer.

4. The method of claim 1, wherein the smooth muscle cells and endothelial cells are human induced pluripotent stem cell derived.

5. The method of claim 1, wherein the smooth muscle cell gel is injected coaxially using a needle.

6. The method of claim 1, wherein the smooth muscle cell gel and the endothelial cell gel are both extruded from different compartments of the same coaxial needle.

7. The method of claim 1, wherein the second inner layer is formed after the first inner layer.

8. The method of claim 1, wherein the blood vessel has high elasticity and has a rough surface.

9. A method for producing a blood vessel comprising:

printing an outer layer;

removing a polyvinyl alcohol component from the outer layer to produce an elastic outer layer;

forming a first inner layer comprised of smooth muscle cells comprised of smooth muscle cell gel comprised of smooth muscle cells, fibrinogen, and thrombin; and forming a second inner layer comprised of an endothelial cell gel comprised of endothelial cells, fibrinogen, and thrombin, wherein the endothelial cells are first mixed with a fibrinogen solution and then coaxially extruded with the thrombin, and wherein the first inner layer is between the elastic outer layer and the second inner layer.

10. The method of claim 9, wherein the smooth muscle cells are first mixed with a fibrinogen solution and then coaxially extruded with the thrombin.

11. The method of claim 9, wherein the polyvinyl alcohol is removed by immersing the elastic outer layer in deionized water.

12. The method of claim 9, wherein the outer layer is comprised of a biodegradable elastomer.

13. The method of claim 9, wherein the smooth muscle cells and endothelial cells are human induced pluripotent stem cell derived.

14. The method of claim 9, wherein the smooth muscle cell gel is injected coaxially using a needle.

15. The method of claim 9, wherein the smooth muscle cell gel and the endothelial cell gel are both extruded from different compartments of the same coaxial needle.

16. The method of claim 9, wherein the second inner layer is formed after the first inner layer.

17. The method of claim 9, wherein the blood vessel has high elasticity and has a rough surface.

* * * * *